United States Patent [19]

Meacham, Jr. et al.

[11] 4,102,645
[45] Jul. 25, 1978

[54] STERILIZATION APPARATUS

[75] Inventors: Thomas E. Meacham, Jr., Philadelphia; David C. Johnson, Ambler, both of Pa.

[73] Assignee: Refreshment Machinery Incorporated, Warminster, Pa.

[21] Appl. No.: 699,026

[22] Filed: Jun. 23, 1976

[51] Int. Cl.² ............................................. A61L 3/00
[52] U.S. Cl. ............................ 21/102 R; 21/DIG. 2; 21/54 R; 250/428; 250/432 R; 250/435
[58] Field of Search ............ 21/DIG. 2, 54 R, 102 R; 426/248; 99/451; 250/428, 432 R, 435

[56] References Cited

U.S. PATENT DOCUMENTS

| | | | |
|---|---|---|---|
| 1,723,603 | 8/1929 | Chesney | 426/248 |
| 2,301,315 | 11/1942 | Opp | 21/102 R |
| 3,535,513 | 10/1970 | Cirami | 21/DIG. 2 UX |
| 3,589,862 | 6/1971 | Veloz | 21/102 R |
| 3,634,025 | 1/1972 | Landry | 21/102 R |
| 3,659,096 | 4/1972 | Kompanek | 21/54 R |
| 3,825,494 | 7/1974 | Call et al. | 21/DIG. 2 |
| 3,904,363 | 9/1975 | Free | 21/102 R |

FOREIGN PATENT DOCUMENTS

| | | | |
|---|---|---|---|
| 676,456 | 7/1952 | United Kingdom | 99/451 |
| 687,388 | 2/1953 | United Kingdom | 21/DIG. 2 |

*Primary Examiner*—Barry S. Richman
*Attorney, Agent, or Firm*—Seidel, Gonda & Goldhammer

[57] ABSTRACT

Liquid flowing through a housing is sterilized by being subjected to radiation which passes through a window transparent to ultraviolet rays. The liquid is prevented from contacting the window by an air pocket. The air in the pocket is maintained by introducing air into the liquid which either replenishes air absorbed from the pocket by the liquid at the air-water interface or prevents the liquid from absorbing air from said pocket.

5 Claims, 3 Drawing Figures

STERILIZATION APPARATUS

BACKGROUND

It is believed that the subject matter of the present invention is classifiable in class 426/248 and/or class 21/102.

For relevant prior art, see U.S. Pat. No. 3,589,862. As pointed out in that patent, it is highly undersirable to permit direct contact from the liquid being treated and the window transparent to radiation due to the fact that such direct contact results in mineral deposits on the window which interferes with proper transmission of the radiation to the liquid. The solution disclosed in said patent includes an inflatable bag to confine the liquid. However, such inflatable bag does not solve the problem since the bag over a period of time will have mineral deposits accumulated on its inner surface and will therefore also be subjected to the problem sought to be overcome, namely the prevention of deposited minerals which interfere with transmission of ultraviolet rays to the liquid being treated.

The present invention utilizes an air pocket as the sole means for preventing direct contact between the liquid and the window transparent to radiation, with air being introduced into the liquid to maintain the pocket and thereby prevent the accumulation of mineral deposits on any surface which would interfere with the transmission of ultraviolet rays.

SUMMARY OF INVENTION

The apparatus for sterilizing a liquid in accordance with the present invention includes a housing having a chamber therein and provided with an inlet and outlet through which a liquid is adapted to flow. A radiation means for sterilizing the liquid while the liquid is in said chamber is provided. A window transparent to radiation is disposed between the sterilizing means and the chamber.

The present invention includes means for producing and for maintaining an air pocket between said window and any liquid in the chamber to prevent direct contact between the liquid and the window without using a barrier between the air pocket and the liquid.

A method in accordance with the present invention includes introducing a liquid into a chamber and treating the liquid while the liquid is in the chamber by radiation. The method contemplates providing a window transparent to radiation between the liquid being treated and the source of radiation while using an air pocket to prevent direct contact between the liquid and the window. The method further contemplates introducing air into the liquid to maintain said air pocket either by replenishing the pocket to compensate for air absorbed by the liquid at the air-water interface or to prevent the liquid from absorbing air at said interface.

It is an object of the present invention to provide apparatus and method which utilizes an air pocket as a buffer zone between liquid being sterilized and a window transparent to radiation while overcoming a tendency of air to be lost from the pocket by being absorbed at the air-liquid interface.

It is another object of the present invention to provide and maintain an air pocket buffer zone in sterilizing apparatus in a manner which is simple, inexpensive and reliable.

Other objects will appear hereinafter.

For the purpose of illustrating the invention, there is shown in the drawings a form which is presently preferred; it being understood, however, that this invention is not limited to the precise arrangements and instrumentalities shown.

Referring to the drawing in detail, wherein like numerals indicate like elements, there is shown in FIG. 1 an apparatus for practicing the present invention designated generally as 10.

Figure 1:
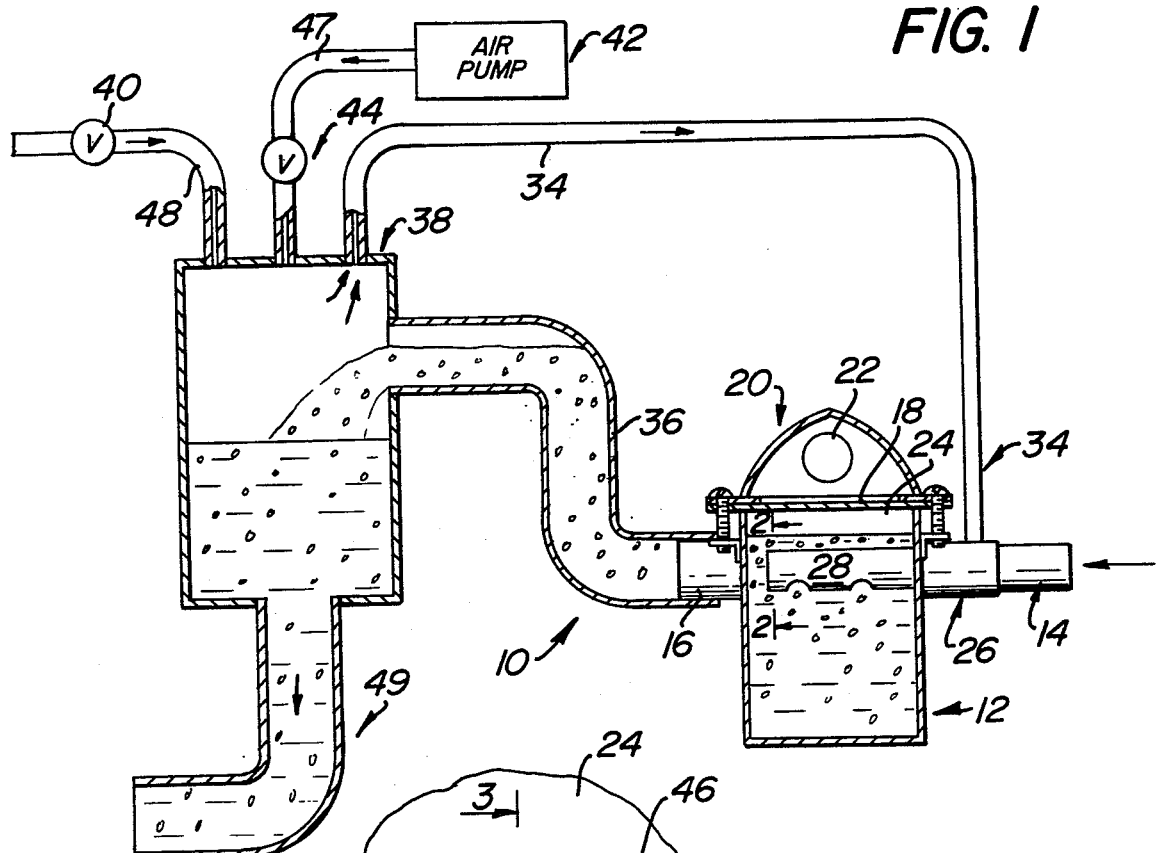
FIG. 1 is a diagrammatic illustration of apparatus in accordance with the present invention.
Figure 2:
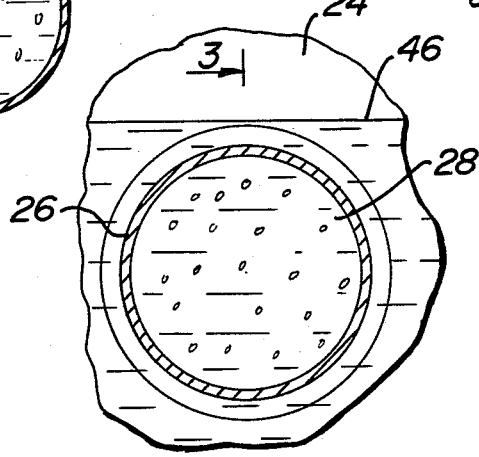
FIG. 2 is a sectional view taken along the line 2—2 in FIG. 1.

The apparatus 10 includes a housing 12 provided with an inlet conduit 14 and an outlet conduit 16. The housing 12 supports a window 18 transparent to ultraviolet rays. A cover 20 overlies the window 18. Between the window 18 and cover 20, there is provided a source of radiation such as a bulb for emitting ultraviolet rays having a wave length at least as low as 2537 A. Bulb 22 may be provided with a reflector thereabove or the inner surface of the cover 20 may be a reflector surface so that the ultraviolet rays are directed downwardly through the window 18 to the liquid to be sterilized.

The present invention contemplates an air pocket 24 as the sole means between the window 18 and the liquid to be sterilized within the housing 12. The pocket 24 prevents any direct contact between the liquid and the window 18. Since there is tendency for air to be absorbed by the liquid at the air-liquid interface 46, a means is provided to maintain the air pocket 24. The elevation of outlet 16 determines the elevation of interface 46 so that the height of pocket 24 is uniform.

Inlet conduit 14 is provided with an adaptor 26 which extends into the housing 12. In the preferred embodiment as illustrated, the inlet conduit 14, adaptor 26 and outlet conduit 16 may be coaxial, but the distance from the adaptor 26 and the outlet conduit should be as great as the design allows.

Figure 3:
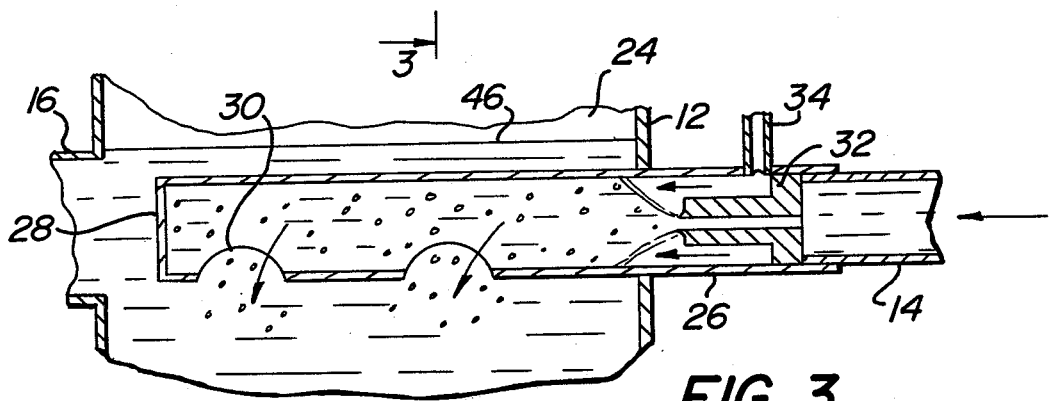
FIG. 3 is a sectional view taken along the line 3—3 in FIG. 2.

The adaptor 26 has one end connected to conduit 14 and its other end 28 is closed. Discharge from within the adaptor 26 into the housing 12 is by way of one or more openings 30 on the lower surface of the adaptor 26. See FIG. 3.

The adaptor 26 at the end adjacent inlet conduit 14 is provided with a venturi 32. On the suction side of the venturi 32, one end of conduit 34 communicates with the adaptor 26 for introducing air into the liquid.

As shown in FIG. 1, the conduit 36 has one end connected to the outlet conduit 16. The other end of conduit 36 is connected to an air-water separator 38. The other end of conduit 34 is connected to the air-water separator 38 adjacent the air zone at the upper end thereof. Conduit 47 has one end connected to the airwater separator 38. The other end of conduit 47 is connected to an air pump 42. Conduit 47 is provided with a selectively operable valve 44. Conduit 48 has one end connected to the air-water separator 38. The other end of conduit 48 is open to the atmosphere. Conduit 48 is provided with a selectively operable valve 40. Conduit 49 is connected to the air-water separator 38 adjacent to the water zone at the lower end thereof.

Pump 42 is an air pump which may be regulated to introduce air into the air-water separator at a controlled rate as a function of the amount of air permanently dissolved into the water which is not recovered in the air-water separator 38. The air pump 42 may be the typical air pump used for aerating an aquarium, or any source of compressible gas, such as bottled air.

If an air separator 38 is provided downstream from the housing 12, and air is recirculated by way of conduit 34 from the air-water separator 38, there is the advantage that the recirculated air has already been treated with ultraviolet radiation. If there is no air-water separator 38 downstream from the housing 12 and/or when system pressure is equal to or above atmospheric pressure, it is preferred to introduce the air into the adaptor 26 by the pump 42. Air may be drawn from the atmosphere through conduit 34 to adaptor 26 when the system pressure is at or below atmospheric pressure.

Any one of a wide variety of materials may be utilized for the window 18. For example, the window 18 may be quartz, transparent Teflon, etc. The diameter of the outlet conduit 16 is preferably greater than the diameter of the inlet conduit 14 so that the upper edge of the outlet conduit 16 defines the elevation of the air-liquid interface 46. If desired, the housing 12 may be provided with a pair of outlet conduits whose combined flow capacity is greater than that of the inlet conduit 14.

The apparatus 10 operates as follows:

Initially, it will be assumed that the valve 44 is closed, the pump 42 is shut off, and valve 40 is open. Water under pressure is introduced by way of conduit 14 through the adaptor 26 and discharges downwardly into the housing 12 by way of the opening 30. Suction from the venturi 32 causes air to flow from a source at ambient temperature and pressure through conduit 34 and to be intimately mixed with the water at the venturi 32 and/or when discharged through opening 30.

The rate of flow air through conduit 34 to the venturi 32 is a direct function of line pressure and will vary directly with such line pressure. The air introduced into the water will prevent the water from absorbing air from the air pocket 24 at the air-water interface 46 thereby maintaining the air pocket 24 intact. The air in pocket 24 is at a slightly higher pressure and acts as a barrier to prevent direct contact between the liquid and the window 18. As the liquid flows through the housing 12 and out outlet conduit 16, it is sterilized or otherwise treated by exposure to ultraviolet radiation from source 22. Any air absorbed from the pocket 24 at the air-water interface 46 is replenished by the air introduced into the water at the venturi 32.

When the line pressure of the liquid in conduit 14 is so low as to render venturi 32 inefficient or when there is no air-water separator 38 downstream from the housing 12, air is introduced to the venturi 32 from pump 42 at a controlled rate so as to obtain an optimum ratio of one part air to twenty parts water by volume. If separator 38 is operating at a pressure above atmospheric and an excess amount of air is being dissolved into the water at separator 38, pump 42 may be operated to replenish that air loss. The apparatus 10 operates continuously to introduce air into the liquid being processed so as to maintain the integrity of the air pocket 24 without utilizing any barrier between the liquid and window 18 while at the same time preventing any direct contact between the liquid and window 18.

The present invention may be embodied in other specfic forms without departing from the spirit or essential attributes thereof and, accordingly, reference should be made to the appended claims, rather than to the foregoing specification as indicating the scope of the invention.

We claim:

1. Apparatus for sterilizing a liquid with radiation comprising a housing having a chamber provided with an inlet, an outlet in the side wall of the housing adjacent the upper end thereof and through which liquid may exit from said chamber, means for sterilizing a liquid by radiation while the liquid is in said chamber, a window transparent to radiation from said sterilizing means, means associated with said inlet for discharging the liquid downwardly into the chamber in a direction away from the window, said window being disposed below said sterilizing means so that radiation may enter said chamber, said window defining the upper limit of said liquid in said chamber, and means for producing and maintaining an air pocket between said window and the upper surface of any liquid in said chamber to prevent direct contact between the liquid and said window without using a barrier between the air pocket and the liquid.

2. Apparatus in accordance with claim 1 wherein said lastmentioned means includes a venturi upstream of the chamber for introducing air into the liquid prior to the liquid being introduced in said chamber.

3. Apparatus in accordance with claim 1 including an adaptor connected to said inlet, said adaptor extending into said chamber, said adaptor having a discharge port directed downwardly away from said window, said last-mentioned means including a venturi forming a part of said adaptor and a conduit connected to said venturi for introducing low pressure air into the liquid at said venturi.

4. Apparatus in accordance with claim 1 wherein said last mentioned means includes a venturi located upstream of the chamber and operatively connected to said inlet, and an air pump connected to the venturi for introducing air into the liquid before the liquid enters said chamber.

5. Apparatus for sterilizing liquid with radiation comprising a housing having a chamber provided with an inlet, an outlet in the side wall of the housing adjacent the upper end thereof and through which liquid may exit from said chamber, an outlet conduit connected to said outlet, means for sterilizing a liquid by radiation while the liquid is in said chamber, a window transparent to radiation from said sterilizing means, said window being disposed below said sterilizing means so that radiation may enter said chamber, said window defining the upper limit of said liquid in said chamber, means for producing and maintaining an air pocket between said window and the upper surface of any liquid in said chamber to prevent direct contact between the liquid and said window without using a barrier between the air pocket and the liquid and an air separator communicating with said outlet conduit for separating air treated by said sterilizing means from liquid as they flow through said separating means, said air separating means being in communication with said means for producing and maintaining an air pocket whereby replenishment of air to the air pocket is accomplished by using presterilized air.

* * * * *